United States Patent
Shimizu et al.

(10) Patent No.: US 6,547,825 B1
(45) Date of Patent: Apr. 15, 2003

(54) ARTIFICIAL TRACHEA

(75) Inventors: Yasuhiko Shimizu, 39-676, Kohataogurayama, Uji-shi, Kyoto (JP), 611-0002; Tatsuo Nakamura, Kyoto (JP)

(73) Assignees: Yasuhiko Shimizu, Kyoto (JP); Tapic International Co., Ltd., Tokyo (JP)

( * ) Notice: Subject to any disclaimer, the term of this patent is extended or adjusted under 35 U.S.C. 154(b) by 0 days.

(21) Appl. No.: 10/089,931

(22) PCT Filed: Sep. 29, 2000

(86) PCT No.: PCT/JP00/06760

§ 371 (c)(1),
(2), (4) Date: Apr. 3, 2002

(87) PCT Pub. No.: WO01/24731

PCT Pub. Date: Apr. 12, 2001

(30) Foreign Application Priority Data

Oct. 4, 1999 (JP) .............................................. 11-282561

(51) Int. Cl.⁷ .................................................. A61F 2/02
(52) U.S. Cl. .................................................. 623/23.64
(58) Field of Search .................... 623/23.64, 23.65, 623/23.69, 23.7, 23.75, 23.72, 1.13, 1.122, 1.35, 1.44, 1.46, 1.45, 1.47, 1.49, 1.5, 1.51

(56) References Cited

U.S. PATENT DOCUMENTS

| | | | | |
|---|---|---|---|---|
| 3,105,492 A | * | 10/1963 | Jeckel | 623/1.44 |
| 4,629,458 A | * | 12/1986 | Pinchuk | 623/1.33 |
| 5,002,583 A | * | 3/1991 | Pitaru et al. | 623/11.11 |
| 5,157,111 A | * | 10/1992 | Pachence | 128/DIG. 8 |
| 5,236,447 A | * | 8/1993 | Kubo et al. | 623/1.13 |
| 5,413,597 A | * | 5/1995 | Krajicek | 128/DIG. 8 |
| 5,733,337 A | * | 3/1998 | Carr et al. | 435/325 |
| 5,948,654 A | * | 9/1999 | Tranzuilloo et al. | 424/422 |
| 6,136,024 A | * | 10/2000 | Shimizu | 623/1.47 |
| 6,335,029 B1 | * | 1/2002 | Kamath et al. | 424/422 |

* cited by examiner

*Primary Examiner*—David J. Isabella
(74) *Attorney, Agent, or Firm*—Edwards & Angell; David G. Conlin; Edward J. Adamson

(57) ABSTRACT

The present invention has an object to provide an artificial trachea that is able to be used safely in the clinical application, and especially an artificial trachea for the intrathoracic trachea, and the artificial trachea comprises a polypropylene mesh tube for the base material, around the outer periphery of which a polypropylene filamentous stent is wound in a spiral shape, an amorphous collagen thin layer formed on the surface of the base material, and a fine fibrous collagen layer (20) formed on the inner and outer surface of the amorphous collagen thin layer, to which thermal dehydration crosslinking is performed.

3 Claims, 3 Drawing Sheets

ARTIFICIAL TRACHEA

TECHNICAL FIELD

The present invention relates to an artificial trachea for a trachea, and more particularly, to an artificial trachea used as a trachea substitute for the intrathoracic trachea.

BACKGROUND ART

In recent years, accompanying the progress made in anesthesia control and post-operative control, including operative procedure for malignant tumors of organs in the cervical and thoracic parts, there has been an increase in the number of occasions in which it is necessary to reconstitute the trachea or tracheal bifurcation.

Although the most clinically reliable reconstruction methods are direct anastomoses such as end-to-end anastomosis and end-to-side anastomosis, these methods are subject to their own restrictions on the range of reconstruction, and even within the allowed range, high-degree anastomotic techniques and relaxation sutures, etc. are required. Consequently, these procedures tend to be associated with extensive invasion. At that time, the use of a trachea substitute made of an artificial material (hereinafter to be referred to as an "artificial trachea") enables reconstruction to be performed easily and as a result, the indications for this operation can naturally be expected to be expanded.

Attempts in applying such an artificial trachea began with animal experiments conducted by Daniel, R A Jr. (published in *J. Thorac. Surg.* 17, 335 (1948) "The Regeneration of Defects of the Trachea and Bronchi"), and although various materials have been attempted to be used since that time, no artificial materials that can be sued safely in the clinical application have been still developed with the exception of partial prosthesis of the cervical trachea.

In the case of artificial trachea for the intrathoracic trachea for which there is the greatest desire for clinical effectiveness in particular, differing from replacement of the cervical trachea in which the artificial trachea is densely covered by surrounding tunica muscularis following replacement, since the artificial trachea is subjected to poor conditions in which there is little support and continuously subjected to the application of external force, in addition to common problems confronting artificial trachea in the form of providing adequate support and rapid and reliable incorporation in the body with little inflammatory reaction, countermeasures against leakage of air constitute the most serious problem.

DISCLOSURE OF INVENTION

In order to improve the situation as described above, the object of the present invention is to provide an artificial trachea that is able to be used safely in the clinical application, and especially an artificial trachea for the intrathoracic trachea.

The present invention is an artificial trachea which comprises a polypropylene mesh tube 21 for the base material, around the outer periphery of which a polypropylene filamentous stent 22 is wound in a spiral shape, an amorphous collagen thin layer 30 formed on the surface of said base material, and a fine fibrous collagen layer 20 formed on the inner and outer surface of said amorphous collagen thin layer, to which thermal dehydration crosslinking is performed. (A simplified drawing of the overall constitution is shown in FIG. 1. Furthermore, in the drawing, although those members indicated with reference numerals 21, 22 and 30 should be indicated as being cross-sections with diagonal lines, such diagonal lines are omitted due to their complexity.)

Here, the thin layer formed on the surface of the base material not only covers the surface of the mesh units constituting the mesh tube, but also obstructs the pores in the mesh and covers the surface of the filamentous stent.

In addition, the amorphous collagen layer refers to a collagen layer having an amorphous structure in which collagen molecules are irregularly dispersed in the monomer and oligomer states.

Moreover, as shown in FIG. 2, the fine fibrous collagen layer refers to that in which ultrafine fibers 15 having a diameter of about 5 nm and composed of several collagen molecules serve as the basic unit for forming fine fibers 14 having a diameter of about 50 nm, these then form narrow fibers 13a and 13b having a diameter of about 2 µm, said narrow fibers then alternately overlap in the manner of weft and warp to form fibers 12 having a diameter of about 6 µm, these fibers then overlap in the coaxial direction to form plate-like fibers 11 having a diameter of about 20–50 µm, and said plate-like fibers are dispersed in the form of a non-woven fabric (see reference numeral 20). The overall constitution of this layer is shown in FIG. 3.

Furthermore, the above artificial trachea is suitable for use as an intrathoracic trachea, and particularly as a trachea substitute for the tracheal bifurcation. Furthermore, it can naturally also be used as a trachea substitute for the cervical trachea based on the degree of difficulty of that application.

Figure 1:
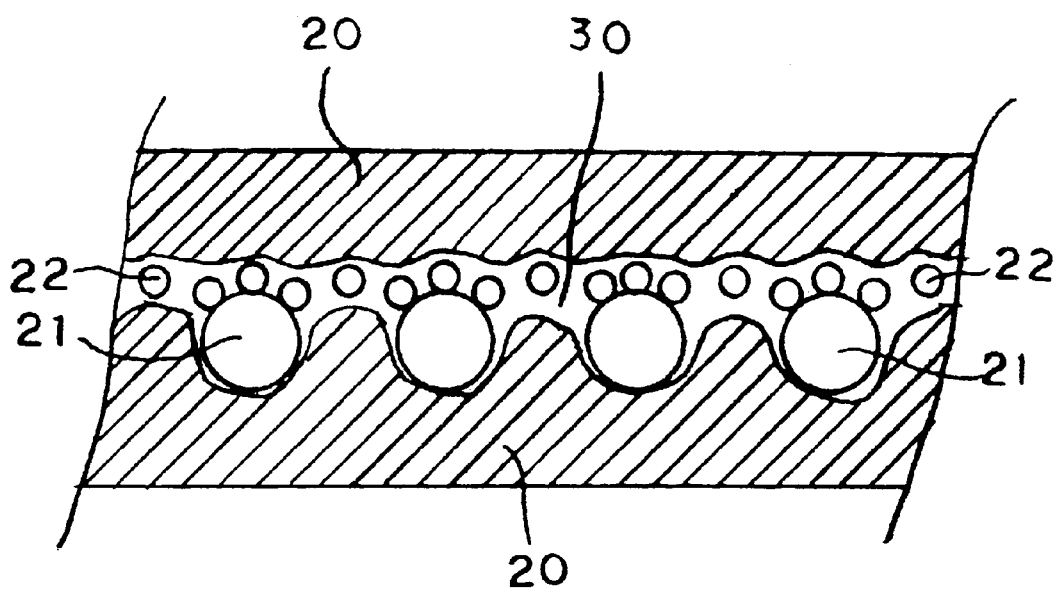
FIG. 1 is a cross-sectional view schematically showing the wall structure of the artificial trachea of the present invention.
Figure 2:
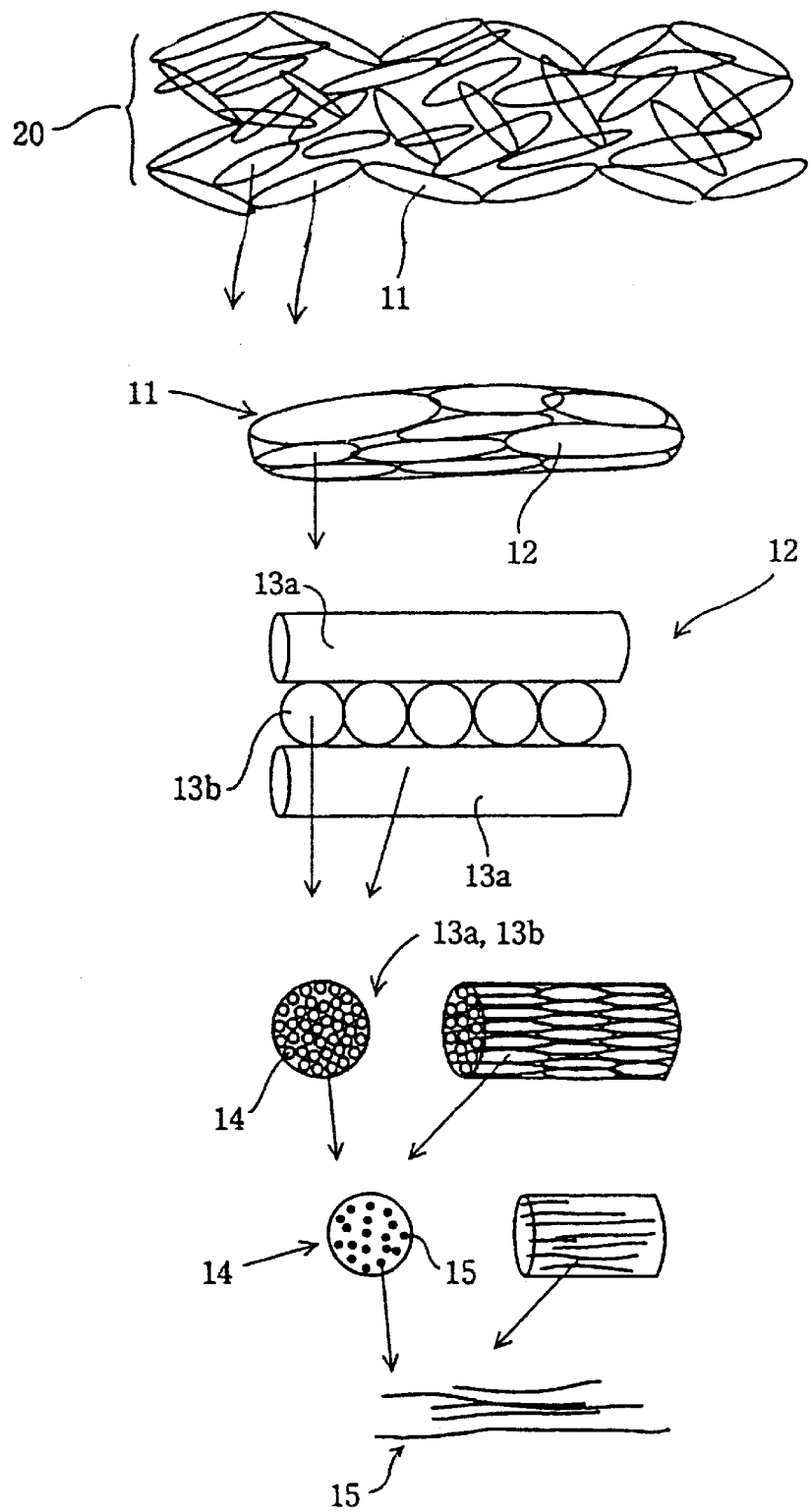
FIG. 2 is a drawing schematically showing the multi-element structure of the fine fibrous collagen layer of the present invention.
Figure 3:
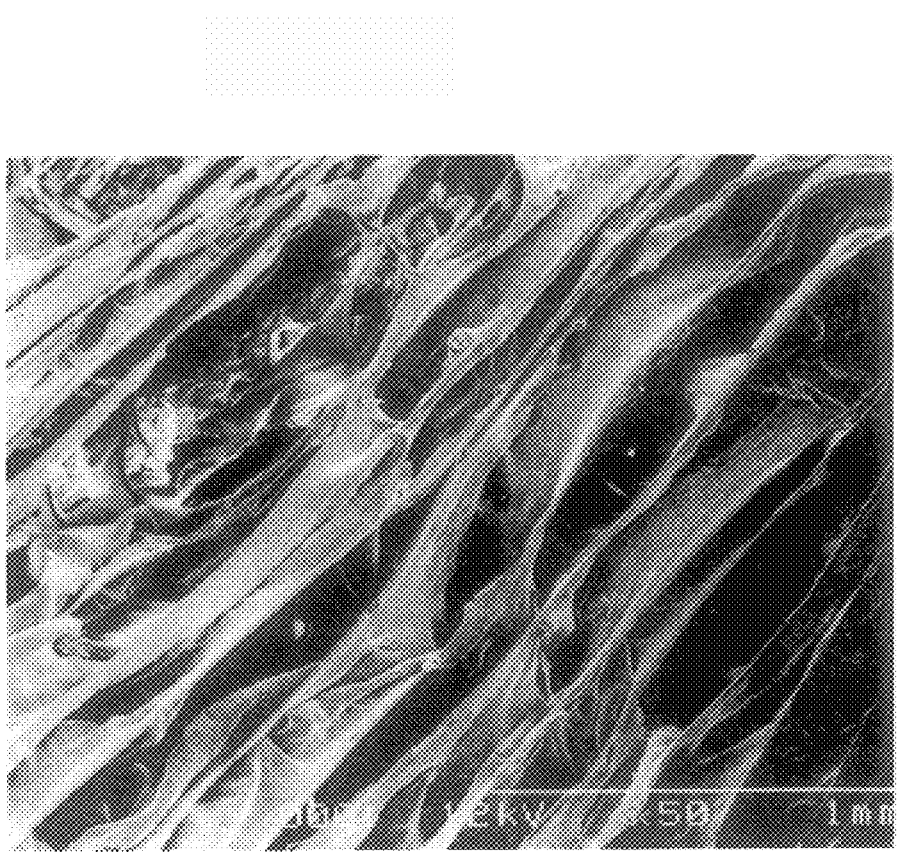
FIG. 3 is a drawing schematically showing the overall constitution of the fine fibrous collagen layer of the present invention (photo substituting for drawing).

Here, each of the reference numerals used represent the following constituent elements.

11: Plate-like fibers
12: Fibers
13a: Narrow fibers
13b: Narrow fibers
14: Fine fibers
15: Ultrafine fibers
20: Fine fibrous collagen layer
21: Mesh tube
22: Stent
30: Amorphous collagen thin layer

BEST MODE FOR CARRYING OUT THE INVENTION

To begin with, with respect to the raw material, although various kinds of collagen used in the prior art can be used for the collagen, examples of which include neutral-solubilized collagen, acid-solubilized collagen, alkaline-solubilized collagen and enzyme-solubilized collagen, enzyme-solubilized collagen that has been treated with an enzyme such as pepsin, trypsin, chymotrypsin, papain or pronase is preferable. This is because the telopeptide serving as the antigen group in the collagen molecule is effectively removed, thereby eliminating nearly all of its antigenicity.

There are no particular restrictions on the origin of this collagen, and type I collagen or a mixture of type I collagen and type III collagen obtained by extraction and purification from the skin, bone, cartilage, tendon, viscera and so forth of cows, pigs, rabbits, sheep, kangaroos, birds, fish and other animals can be used.

On the other hand, with respect to the mesh tube serving as the constituent material of the base material, an example of a preferable material is soft Marlex® mesh (knitted polypropylene mesh having a pore size of about 300 μm manufactured by Bard) based on previous results. The polypropylene stent that is the other constituent material of the base material serves as a lumen support of the said mesh tube, and after winding around the outer surface of said mesh tube in a spiral shape and at a suitable pitch, the stent should be fusion-bonded by heating and sutured with suture such as 5-0 Prolene® (trade name) to integrally fasten to said mesh tube.

Next, with respect to the manner of producing the artificial trachea, production should typically be carried out in the manner described below.

(1) Prepare a mesh tube reinforced with stent.
(2) Irradiate said tube with plasma to enhance the affinity with collagen.
(3) Build up a roughly 1 N hydrochloric acid solution of collagen (pH=about 3, collagen concentration: about 0.5–3 wt %, and preferably about 1 wt %) to the surface of said tube. (As a specific method for achieving this, said tube should be immersed in said collagen hydrochloric acid solution, and the mesh pores of said tube should naturally be obstructed.)
(4) Air dry the tube builded up with said collagen (to form an amorphous collagen thin layer).
(5) Place said tube, into the lumen of which an inner die (having an overall outside shape that matches the shape of said tube and an outer diameter that is about 7–10 mm narrower than the inner diameter of said tube, an example of which is a rod or tube), has been inserted in an outer die (having an overall inside shape that matches the shape of said tube and a tubular portion of a diameter that is about 7–10 mm larger than the outer diameter of said tube), and introduce said collagen hydrochloric acid solution into the cavities between said dies and the outside and inside of said tube. During this procedure, as a result of re-dissolving the surface layer of the above amorphous collagen thin layer (the interface with the collagen hydrochloric acid solution introduced in this procedure), the collagen introduced in this procedure is ultimately integrated into a single unit with said thin layer.
(6) Freeze said introduced collagen hydrochloric acid solution (at about −10 to −196° C., and preferably about −20° C.) and after maintaining this state for a predetermined amount of time (about 6–48 hours, and preferably 24 hours), freeze-dry under a vacuum (at about −40 to −80° C., and preferably about −80° C., for about 24–48 hours, and preferably about 48 hours). Fine pieces of ice are formed between the collagen molecules dispersed in the hydrochloric acid solution by the freezing procedure of this step (including the time during which that state is maintained), phase separation occurs in the collagen hydrochloric acid solution, and fine fibers are formed due to the realignment of collagen molecules. Next, in addition to vaporizing the ice present between the collagen molecules during the freeze-drying procedure, said fine fibrous collagen is arranged pluralistically resulting in the formation of the previously mentioned fine fibrous collagen layer.
(7) Perform thermal dehydration crosslinking under a vacuum on said fine fibrous collagen layer (at about 105–150° C. and preferably about 140° C., for about 6–48 hours, and preferably 24 hours). This is to ensure that said fine fibrous collagen layer remains in the body until replacement of the inside and outside of the artificial trachea with the subject's own tissue is completed.

TEST EXAMPLE 1

Polypropylene stent (diameter: 1.0 mm) was wound around the outer periphery of a tube (primary trachea side: inner diameter of 20 mm and length of 40 mm; bronchi sides: inner diameter of 15 mm and length of 20 mm, respectively) comprised of Marlex® mesh (manufactured by Bard, knitted polypropylene mesh having a pore size of about 300 μm) in a spiral shape (pitch: 5 mm) and fusion-bonded by heating, the surface of said mesh tube sutured to the tube with 5-0 Prolene® (manufactured by Azwell) was made to be hydrophilic by irradiating with plasma radiation, and a hydrochloric acid solution of enzyme-solubilized collagen (pH=3.0, collagen concentration: 1.0 wt %) was applied to the surface thereof followed by air-drying to form an amorphous collagen thin layer on the surface of said mesh tube (and the mesh pores of said tube were visually confirmed to be obstructed). Said tube having an amorphous collagen thin layer on said surface, into the lumen of which a rod serving as an inner die (having a diameter of 10 mm on the primary trachea side and 5 mm on the bronchi sides) was inserted, was housed in an outer die (gap between said outer die and the outside of said tube: 5 mm, and extending over the entire circumference of said tube), the above collagen hydrochloric acid solution was introduced into the cavities between the inside and outside of said dies and said tube, and after freezing said introduced collagen hydrochloric acid solution (at about −20° C. for 24 hours), the tube was freeze-dried under a vacuum (at about −80° C. for 24 hours) followed by thermal dehydration crosslinking treatment under a vacuum (at about 140° C. for 12 hours) to obtain an artificial trachea for use as a trachea substitute for a tracheal bifurcation.

The resulting artificial trachea was then applied to the tracheal bifurcation of eleven beagle dogs having body weights of 9–13 kg, respectively. (The trachea and primary bronchus were sutured to the artificial trachea of the present invention by end-to-end anastomosis using 3-0 Vicryl® in interrupted sutures. Here, a silicone stent was inserted into the lumen of said artificial trachea and fixed to the inner surface thereof by suturing as a countermeasure for preventing from infections. Furthermore, the entire artificial trachea was covered using the greater omentum.) After closing the chest, a thoracic drain was removed just after confirming no air leakage. After operation, antibiotic was administered by intramuscular injection for 1 week followed by oral administration of antibiotic until removal of the silicone stent (30 days later).

As a result, 8 of the 11 animals demonstrated longterm survival following observation after operation for a maximum of 10 months (the three animals that died following operation consisted of one animal that died due to the formation of a fistulae in the bronchus, one animal that died due to an accident with anesthesia, and one animal that died due to unknown cause). According to the results of observation of the long-term surviving animals using a bronchoscope, it was observed that the inside of the artificial trachea was covered with glossy, white epithelium, and there was no stricture or formation of granulation in the respiratory tract. Light microscopy and electron microscopy observations revealed the inside of the artificial trachea to be covered with respiratory tract epithelium having cilia.

TEST EXAMPLE 2

An artificial trachea was produced in the same manner as Test Example 1 with the exception of using the artificial trachea of the present invention as a trachea substitute for an intrathoracic trachea (inner diameter: 20 mm, length: 40 mm), and applied in seven beagle dogs having body weights of 9–13 kg, respectively. The animals were sacrificed for observation at 3 months after operation (3 animals), 6 months after operation (3 animals) and 12 months after operation (1 animal), respectively. Stricture or formation of granulation in the respiratory tract was not observed in any of the animals (using a bronchoscope). In addition, light microscopy and electron microscopy observations revealed the inside of the artificial trachea to be covered with respiratory tract epithelium having cilia.

Industrial Applicability

According to the artificial trachea of the present invention, it can be used safely even in the tracheal bifurcation since it is able to promote regeneration of ciliated epithelium of the respiratory tract and does not result in stricture or formation of granulation in the respiratory tract.

We claim:

1. An implantable artificial trachea comprising a polypropylene mesh tube having inner and outer surfaces, said tube having a polypropylene filamentous stent spirally wound on said outer surface, a thin layer of amorphous collagen formed on the mesh tube and stent, and a fine fibrous collagen layer formed on the inner and outer surfaces of said thin layer of amorphous collagen, wherein the collagen is subjected to thermal dehydration crosslinking.

2. The artificial trachea according to claim 1, wherein the artificial trachea is used as a substitute for an intrathoracic trachea.

3. The artificial trachea according to claim 1, wherein the artificial trachea is used as a substitute for a trachea bifurcation.

* * * * *